United States Patent [19]

McGuire

[11] Patent Number: 5,071,347
[45] Date of Patent: Dec. 10, 1991

[54] DENTAL INSTRUMENT FOR REMOVING SALIVA

[76] Inventor: Jimmie L. McGuire, 2938 Ramble Rd., West, Bloomington, Ind. 47401

[21] Appl. No.: 392,904

[22] Filed: Aug. 14, 1989

[51] Int. Cl.⁵ .................. A61C 17/06; A61C 17/14
[52] U.S. Cl. ..................................... 433/97; 433/94
[58] Field of Search ........................... 433/91, 93, 94

[56] References Cited

U.S. PATENT DOCUMENTS

| | | | |
|---|---|---|---|
| 950,109 | 2/1910 | Leukowicz | 433/91 |
| 1,401,646 | 12/1921 | Ronn | 433/93 |
| 1,742,080 | 12/1929 | Jones | 433/93 X |
| 2,587,008 | 2/1952 | Stadelmann | 433/94 |
| 2,637,106 | 5/1953 | Otis | 433/91 |
| 2,644,234 | 7/1953 | Scott | 433/94 |
| 3,091,859 | 6/1963 | Baughan | 433/94 |
| 3,101,543 | 8/1963 | Baughan | 433/94 |
| 3,148,449 | 9/1964 | Van Lanigan | 433/93 |
| 3,396,468 | 8/1968 | Dayhoff | 433/93 |
| 3,520,300 | 7/1970 | Flower, Jr. | 433/91 X |
| 4,053,984 | 10/1977 | Moss | 433/93 |
| 4,068,664 | 1/1978 | Sharp et al. | 433/91 X |
| 4,215,984 | 8/1980 | Reichley | 433/93 |
| 4,260,378 | 4/1981 | O'Neil | 433/93 |

FOREIGN PATENT DOCUMENTS

| | | | |
|---|---|---|---|
| 761736 | 10/1933 | France | 433/94 |
| 45437 | 5/1935 | France | 433/94 |
| 242045 | 4/1946 | Switzerland | 433/94 |

Primary Examiner—Robert P. Swiatek
Assistant Examiner—Nicholas D. Lucchesi
Attorney, Agent, or Firm—Woodard, Emhardt, Naughton, Moriarity & McNett

[57] ABSTRACT

A dental instrument for removing saliva from a patient's mouth is disclosed that includes a pair of tubes configured to be operatively positioned within the patient's mouth to support a pair of absorbent rolls at the sides of alveolar ridge. One of the tubes terminates at its proximal end in a suction adaptor having a sealing face for contact interface with a suction tube connected to a dental suction device. The proximal end of the other of the tubes intersects the first tube at its mid-length. An absorbent roll supporting perforated stem is removably inserted into the distal end of each of the tubes. Each stem includes a number of apertures in fluid communication with the passageways through the pair of tubes so that suction applied at the suction adaptor operates through the apertures to remove fluid absorbed by the absorbent rolls. An adjustable clamping structure is connected to one of the tubes and is mountable under the jaw of the patient to support the instrument. In one specific embodiment, the absorbent rolls carried by the instrument are composed of a single layer of polyurethane foam. In another embodiment, the instrument is composed of a resilient plastic material to permit flexing of the instrument as the patient moves without disturbing the proper positioning of the instrument about the alveolar ridge. An absorbent roll is disclosed for use with the dental instrument that is composed essentially of a single layer of synthetic sponge or foam material.

3 Claims, 2 Drawing Sheets

DENTAL INSTRUMENT FOR REMOVING SALIVA

BACKGROUND OF THE INVENTION

This invention relates generally to dental instruments for removing or ejecting saliva from the mouth of a patient during a dental procedure. More particularly, the invention concerns an instrument having structure for securely supporting absorbent rolls and for providing suction for ejecting saliva from the patient's mouth when the absorbent rolls are in their operative positions.

In the field of dentistry, it is well known that mucus, saliva and other fluids can accumulate within the mouth of a patient during various dental procedures. Fluid accumulation in the patient's mouth is particularly nettlesome during procedures performed on the lower teeth of the patient, since the fluid has a tendency to invade the work area. Thus, dentists or dental assistants use a variety of methods to absorb and/or remove fluids from the patient's mouth during the course of the dental procedure. In one of the more common methods, a device known in the trade as a Garmers cotton roll holder is used to retain a pair of cotton rolls in engagement about the alveolar ridge on both sides of the teeth of the patient. The cotton rolls absorb the saliva and fluids, keeping the work area around the patient's teeth clear and free from substances that might interfere with the dental procedure. The Garmers device is described in U.S. Pat. No. 2,625,739, which is incorporated herein by reference to illustrate one of the more commonly used dental appliances for removing or ejecting fluids.

While the Garmers absorbent roll holder has become somewhat of a standard within dentistry, it suffers from certain disadvantages that are addressed by the present invention. For instance, the Garmers device can be uncomfortable to the patient since the device is capable of scraping the alveolar ridge, lips, and gums of the patient. In addition, the Garmers device is not generally intended to be a disposable device, primarily because it is too costly for disposal after every use. Another drawback of the Garmers device is that it generally requires alternative means for removing excessive saliva and fluids, such as a suction tube periodically placed within the patient's mouth to remove collected fluids.

This latter difficulty with the traditional Garmers device is addressed in one fashion by various devices illustrated in patents to Cofresi, U.S. Pat. No. 3,049,806, Sommerstein, U.S. Pat. No. 2,950,533, Tofflemire, U.S. Pat. No. 2,791,030, Scott, U.S. Pat. No. 6,244,234, Lampert, U.S. Pat. No.2,180,249, and Baughan, U.S. Pat. No. 3,091,859. Many of the devices described in these patents provide means for removing saliva by a suction tube requiring continuous connection to a suction source during the dental procedure. None of these devices appear to combine suction means with the Garmers device configuration that has gained widespread acceptance and usage as one of the most efficient and practical configurations for retaining cotton rolls in a proper operative position about the teeth work area. In addition, most of these devices are difficult to clean and sterilize, but are not particularly well suited for use as a disposable product.

Other references of interest include the patents to Rosentheiler, U.S. Pat. No. 4,240,789, Fridge, Sr., U.S. Pat. No. 2,914,852, and Larson, et al., U.S. Pat. No. 4,233,025.

SUMMARY OF THE INVENTION

In view of the limitations and disadvantages of the dental instruments of the prior art, a device is provided in the present invention for removing saliva and other fluids from the mouth of a patient. The device comprises a pair of interconnected tubular members adapted for support along the respective sides of the alveolar ridge of the patient's mouth. Each of the pair of tubular members has a proximal end and a distal end and a passageway extending therethrough with an opening at each of the proximal end and the distal end. The pair of tubular members is interconnected such that the proximal end of one of the pair of members intersects the other of the pair of members between the proximal and distal ends of the other member. The fluid passageways of each of the pair of tubular members are in fluid communication. A pair of means are provided for supporting an absorbent roll, each of the means including a hollow stem having an outer wall for engaging the absorbent roll thereabout. A central cavity extends from an open end of the stem with a number of apertures emanating from the cavity passing through the stem and opening at the outer wall. Means are provided for attaching the open end of the stem to one distal end of the tubular members such that the central cavity is in fluid communication with the passageway of the tubular member. An adjustable support affixed to the tubular members is included for engaging under the jaw of the patient to support the device in its operative position. In one aspect of the invention, means are provided at the proximal end of one of of the tubular members for interfacing with a suction device to apply suction through the passageways, the central cavity and the apertures.

An inlet nozzle having a sealing face can be provided at the proximal end of the tubular member against which the suction end of a suction tube connected to the suction device can be pressed to provide intermittent suction to the device. The stem can be removably press-fit into the distal end of the tubular members and can be inserted to varying depths to accommodate various lengths of absorbent rolls supported by the stem. Preferably, however, the stem is fixed in the tubular member by a drop of adhesive.

In another aspect of the invention, the device includes a pair of absorbent rolls each having an inner wall for engaging the outer wall of one of the hollow stems. The absorbent rolls can be composed of a single layer of a foam or a sponge material. In still another aspect of the invention, the device is composed substantially of a resilient material adapted to resiliently flex as the patient moves while maintaining the position of the tubular members relative to the alveolar ridge. The material can be an economically disposable plastic.

It is one object of the invention to provide a dental instrument for removing or ejecting fluids from the mouth of a patient during a dental procedure. It is a further object to provide such a device that uses disposable absorbent rolls and that provides means for suctioning fluids absorbed by the rolls without requiring replacement of the rolls.

Another object is to provide means for suctioning that does not require continuous attachment to a suction hose of a suction device, but permits intermittent interface with the suction device and leaves the area around the patient's mouth free of extraneous tubes. A further object is to provide such a device that is easily deformable yet resilient to permit flexing of the device as the patient moves yet remains in its proper operative position. Yet another object is to make the device comfortable for the patient and to reduce the risk of injury to the patient by its use and still retain the cheek and tongue away from the treatment area. Other objects and advantages of the present invention will be apparent from the following written description and accompanying figures.

DESCRIPTION OF THE PREFERRED EMBODIMENT

Figure 2:
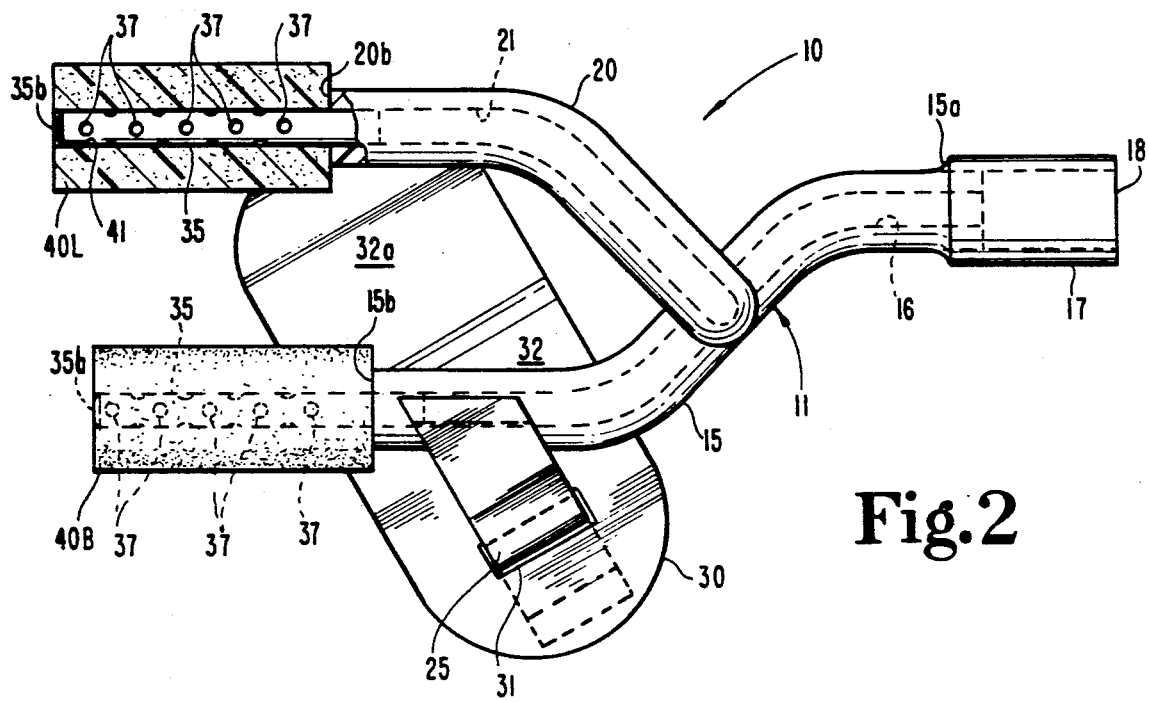
FIG. 2 is a top elevational view of the preferred embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
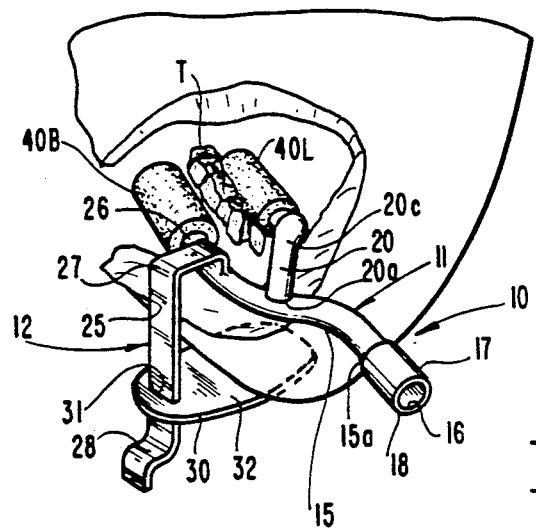
FIG. 1 is a perspective view of the preferred embodiment of the dental instrument of the present invention in operative position within the mouth of a patient.

The dental instrument 10 of the preferred embodiment of the present invention is illustrated in FIG. 1 in its operative position within the mouth of a patient. The instrument 10 includes a tubular structure 11 that is configured to support a pair of absorbent rolls ($40_B$ and $40_L$ in FIG. 1) at the cheek side (buccal) and tongue side (lingual) of the alveolar ridge and, more particularly, a row of teeth T upon which a dental procedure is to be performed. The tubular structure 11 has affixed thereto a clamping structure 12 which is configured to securely clamp the dental instrument 10 to the patient's jaw to support the tubular structure so that the absorbent rolls remain in their operative positions.

It is understood there is both a left side and right side version of the device with the right side only illustrated herein.

The tubular structure 11 includes a primary tube 15 that is gently curved to conform to the outer or buccal side of the row of teeth T. That is, the primary tube 15 has a curvature that generally corresponds to the curvature of the row of teeth T so that one absorbent roll can be positioned between the alveolar ridge and the interior of the cheek of the patient. The primary tube 15 is hollow, that is it includes a fluid passageway 16 along its entire length. Affixed at the proximal end 15a of the primary tube 15 is a suction adapter 17. The suction adapter 17 is configured as a suction nozzle to briefly mate with the suction end of a dental suction device. The suction adaptor 17 in the preferred embodiment has a sealing face 18 against which a suction tube from the suction device can be pressed to apply suction to the instrument 10.

A secondary tube 20 is joined at its proximal end 20a to the primary tube 15 at approximately mid-length of the primary tube. The secondary tube 20 includes a fluid passageway 21 that is in direct fluid communication with the passageway 16 of the primary tube 15. The secondary tube 20 is curved in two planes so that the secondary tube 20 can span the front teeth of the patient at a bridge portion 20c and so that a portion is provided that conforms to the lingual side of the teeth T. The two tubes 15 and 20 are generally parallel at their buccal and lingual locations. As thus configured, the tubular structure 11 provides means for retaining the absorbent rolls directly adjacent the row of teeth T. The primary tube 15 also serves to depress the lower lip of the patient adjacent the front or anterior portion of the mouth. The curved bridge portion 20c of the secondary tube 20 is also supported by the front teeth of the patient, while the portion of the tube adjacent distal end 20b is supported on the floor of the mouth. The geometry of the two tubes also assists in retracting the tongue and cheek of the patient from the working area surrounding the row of teeth T.

The clamping structure 12 includes a mounting arm 25 that is suitably affixed to the primary tube 15 at a joint 26. At the upper portion of the mounting arm 25 is an outwardly projecting flange 27 extending from the joint 26 to provide clearance for the patient's lip when the instrument 10 is in its operative position. As illustrated, the flange 27 holds the lower lip of the patient downwardly and away from the patient's teeth. The mounting arm 25 extends downwardly from the flange 27 terminating at its free end in an outwardly angled ledge 28.

The clamping structure 12 includes a jaw-engaging element or clamp 30 that includes a slot 31 at one end of the clamp through which the mounting arm 25 extends. The slot 31 of the clamp 30 operates in a fashion similar to that described in the Garmers patent, U.S. Pat. No. 2,065,739 in which the slot 31 effectively grips the mounting arm 25 when the jaw engaging clamp 30 is firmly pressed up against the patient's jaw. The jaw engaging clamp 30 includes a gripping surface 32 that is adapted to contact the jaw of the patient to hold the dental instrument 10 in proper position. As shown more clearly in FIG. 3, the jaw engaging clamp 30 or more particularly the surface 32 includes an upwardly angled portion 32a that is adapted to contact the lateral portion of the mandible border. The angled portion 32a is generally directly underlying the two absorbent rolls when the dental instrument 10 is in its proper position. When the device is not in use, the ledge 28 operates as a stop to keep the jaw engaging clamp 30 from becoming disengaged with the mounting arm 25.

Figure 5:
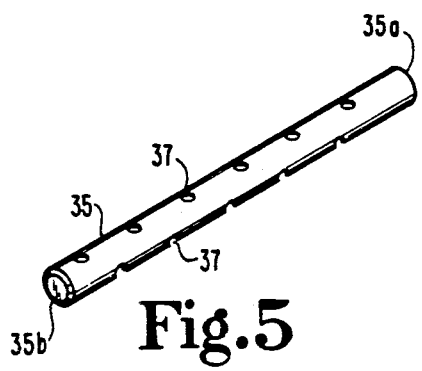
FIG. 5 is a perspective view of the perforated stem shown in FIG. 4.
Figure 4:
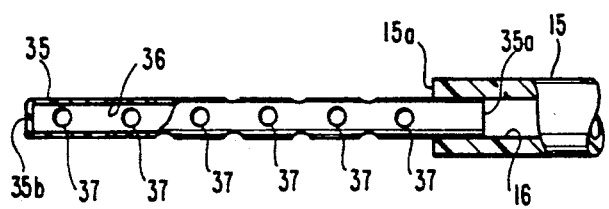
FIG. 4 is a partial cross-sectional view of the perforated stem of the dental instrument engaged within a tube of the instrument shown in FIGS. 1-3.

The absorbent roll supporting feature of the dental instrument 10 of the present invention is shown more clearly with reference to FIGS. 2 and 4. As described above, the primary tube 15 and secondary tube 20 are both hollow, each having a respective passageway communicating entirely therethrough. At the respective distal ends 15a and 20a of the tubes, a perforated stem 35 is pressed into the distal end of each of the passageways 16 and 21 of the primary tube 15 and secondary tube 20, respectively. Each of the perforated stems 35 includes a central cavity 36 opening at the proximal end 35a of the stem that is in direct fluid communication with the fluid passageway, such as passageway 16 of the tube 15, as shown more clearly in FIG. 4. The distal end 35b of the perforated stem is closed so that the central cavity 36 terminates at the distal end. The perforated stem includes a number of apertures 37 through the wall of the stem 35 that communicate directly with the central cavity 36. The apertures 37 can be formed by drilling through the stem 35. In the preferred embodiment, the apertures are staggered along the circumference of the stem 35, as shown in FIG. 5. This placement of apertures optimizes the action of the suction through the apertures to extract as much fluid from the absorbent roll supported by the stem as possible.

In one aspect of the present invention, at least the tubular structure 11 is formed of a relatively easily deformable and resilient material adapted to permit flexing of the tubes. Unlike many of the dental apparatus of the prior art, the primary and secondary tubes 15 and 20 have enough flexibility to accommodate motion of the patient's jaw and mouth when the patient swallows or moves slightly. However, the tubular structure is sufficiently rigid to retain its shape and maintain proper positioning of the absorbent rolls. In the preferred embodiment, the tubular structure 11 is composed of a medical grade plastic, such as polyurethane. The tubular structure 11 is generally transparent to permit direct vision into the respective fluid passageways 16 and 21, for reasons to be described herein. The clamping structure 12 is also preferably composed of a resilient yet strong material, such as plastic or polyurethane, so that the clamping structure 12 is also permitted to flex slightly as the patient moves. Forming the tubular structure 11 and clamping structure 12 of a plastic is more comfortable for the patient to wear. Unlike dental apparatus of the prior art, the instrument 10 of the present invention has no sharp edges to lacerate the cheek, alveolar ridge, tongue or lip of the patient. The comfort of the instrument is also enhanced by the smooth tubular shape of the instrument which is devoid of the sharp edges typical of the flat metal strip structure of the typical Garmers device.

In the preferred embodiment, the perforated stem 35 is glued in passageways 16 and 21; however, if a press fit is used, the outer diameter of the perforated stems 35 is slightly larger than the inner diameter of the fluid passageways, such as passageway 16 of primary tube 15 shown in FIG. 4. Thus, the perforated stem 35 can be easily pressed into the passageway 16; however, there is sufficient frictional engagement that it remains firmly in position during the dental procedure. As a further alternative attachment, a releasable snap fit or other comparable engagement may be provided.

In the case of the removable stem, once the dental procedure is complete, the perforated stem can be readily removed from the distal end 15b or 20b of the primary or secondary tubes. In one embodiment, the primary and secondary tubes have an outer diameter of ¼ inch and the respective fluid passageways have a diameter of approximately ⅛ inch. The perforated stem 35 has an outer diameter of slightly greater than ⅛ inch while the central cavity 36 has a diameter of approximately 1/15 inch. Each of the apertures 37 has a diameter through the outer wall of the perforated stem 35 that is approximately 1/32 inch. The specific lengths and curvatures of the primary and secondary tubes 15 and 20 are generally determined by the physical geometry of the patient's mouth. Since one object of the dental instrument 10 of the present invention is to enhance the comfort of the apparatus to the patient, it is important that the specific dimensions of the tubular structure 11 be adequate for a typical range or group of patients.

Figure 3:
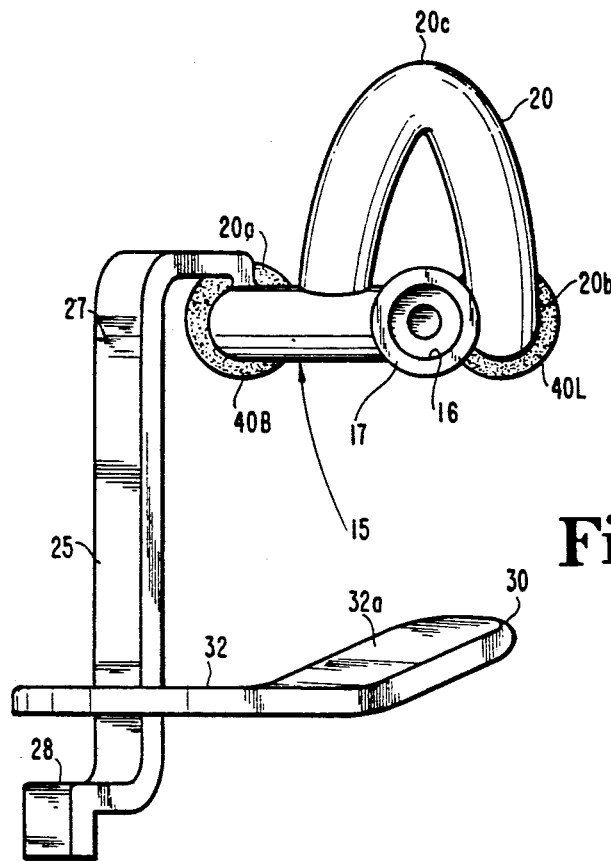
FIG. 3 is a side elevational view of the preferred embodiment of the present invention.

The dental instrument 10 includes a pair of disposable absorbent rolls 40, designated as buccal (B) and lingual (L) rolls in FIGS. 1-3. Each of the rolls is generally cylindrical in shape and includes a hollow interior wall 41, or central passageway, that is adapted to accept a perforated stem 35 therein. Preferably, the diameter of the hollow wall 41 is slightly smaller than the outer diameter of the perforated stem 35 so that a press-fit engagement exists between the absorbent roll 40 and the stem. The stem 35 preferably extends through the entire length of but does not extend beyond the end of the roll 40. Thus, the stem is concealed and less likely to contact the patient's mouth. The stem has a length sufficient to permit variations in the depth of insertion of the stem into the tube passageway in order to accommodate different lengths of absorbent rolls carried by the stem.

In one embodiemtn of the invention, the absorbent roll 40 is a sponge or a foam type material, such as a polyurethane. It should be noted, however, that the absorbent cotton rolls of the prior art may be mounted on the perforated stems 35 of the present invention. Construction of the absorbent roll 40 from a polyurethane material simplifies the construction of the roll in that only a single layer need be manufactured. The polyurethane roll of the present invention is less likely to unravel or need replacing during lengthy dental procedures. The sponge or foam absorbent roll is formed from conventional techniques so that the roll includes a plurality of interstices for communicating fluid from the outer surface of the roll to the hollow wall 41 and central passageway. While the roll is formed from polyurethane in the one specific embodiement, other synthetic material may be suitable that is absorbent and is capable of assuming a sponge or foam configuration.

In the use and operation of the dental instrument 10 of the present invention, one perforated stem 35 is pressed into the distal end 15b of the primary tube 15 and another stem 35 is pressed into the distal end 20b of the secondary tube 20. After the stems have been mounted, an absorbent polyurethane roll 40 is pressed onto each stem. Preferably the rolls 40 are pressed sufficiently far onto the stems 35 to abut the distal ends 15b and 20b of the tubes. With the absorbent rolls 40 in position, the tubular structure 11 is positioned within the patient's mouth with the right side roll $40_L$ positioned at the lingual side of the row of teeth T and the left absorbent roll $40_B$ situated at the buccal side of the row of teeth T. The clamp 30 is adjusted to a snug fit against the patient's jaw so that the dental instrument 10 is firmly positioned about the row of teeth T.

During the dental procedure, saliva and other fluids collecting at the row of teeth T are absorbed by the absorbent rolls $40_L$ and $40_B$. Thus, the working area is kept free of substances that would otherwise impede the dental procedure. Periodically during the dental procedure, it becomes necessary to eject or remove the saliva and fluids from the absorbent rolls 40 since the rolls tend to become saturated after a period of time in the patient's mouth. In a substantial deviation from devices of the prior art, it is only necessary to provide high suction at the suction nozzle 17 at the proximal end 15a of the primary tube 15. Unlike many devices of the prior art, continuous low level suction is not required with the dental instrument 10 of the present invention. Significantly, no tubular connection is required between the instrument 10 and a suction or ejector device. High level suction applied at the suction nozzle 17 is adequate to draw saliva and mucus from the absorbent rolls 40 through the two passageways 16 and 21.

Once the dental procedure is complete, the entire dental instrument 10 may be disposed of, since the instrument is preferably composed of a plastic material. However, if it is desired to reuse the device, cleansing and sterilization of the instrument 10 is made particularly easy by the novel structure of the device. In the cleaning procedure the absorbent rolls 40$_L$ and 40$_B$ are removed from the perforated stems 35. The stems 35 can be removed from the distal ends of the primary and secondary tubes. The hollow stems 35 can be cleansed by passing a disinfectant and sterilizing agent through the open end of the stem into the central cavity and apertures 37. Since the stem 35 is preferably composed of a clear or translucent plastic, direct observation can be used to determine whether further scrubbing is necessary to remove blood or mucous that might have been drawn into the stem 35.

A similar procedure can be employed for the tubular structure 11. Since the tubular structure 11 is open at all ends of the structure, it is relatively easy to inject a cleansing and sterilizing agent at any of the open ends of the passageways 16 and 21. In addition, since the tubular structure 11 is open it is possible to eject blood, mucus or saliva that may collect within the tubes. Moreover, the open-ended configuration of the tubular structure 11 permits the use of a cleaning tool, such as a pipe cleaner type device, to pass completely through the passageways 16 and 21 from end to end of the tubes 15 and 20, respectively. In this manner the dental instrument 10 of the present invention can be easily cleansed and sterilized for reuse if the apparatus is not used as a disposable device.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A device for removing saliva from the mouth of a patient comprising:

a buccal absorbent roll supporting element including a first tube having a proximal end and a distal end, said first tube curved to be supported on the inner portion of the lower anterior lip of the patient with said proximal end outside the mouth of the patient, said first tube having a passageway extending entirely therethrough between said proximal and said distal end of said first tube and a first roll supporting portion adjacent the distal end, the curvature of said first tube and said first roll supporting portion lying substantially in one plane;

a lingual absorbent roll supporting element including a second tube having a passageway extending entirely therethrough between a proximal and a distal end of said second tube, a second roll supporting portion adjacent the distal end and substantially parallel to said first roll supporting portion and lying substantially in said one plane, and a bridge portion spanning between said second roll supporting portion and said proximal end of said second tube, said bridge portion being curved for spanning front teeth of the patient when the device is in operable position within the mouth of the patient, wherein said proximal end of said second tube is connected to said first tube between the proximal and distal ends of said first tube and further wherein the passageway of said second tube is in fluid communication with the passageway of said first tube; and means at the proximal end of said first tube for engaging the suction hose of a suction device for applying suction through the passageways of said first and said second tubes.

2. The device for removing saliva of claim 1, wherein said means for engaging includes means for providing intermittent suction engagement with the suction hose to apply intermittent suction through said passageways.

3. The device for removing saliva of claim 2, wherein said means for providing intermittent suction engagement includes an inlet nozzle having a sealing face against which the suction end of a suction tube connected to the suction device can be intermittently engaged to provide intermittent suction to the device.

* * * * *